United States Patent [19]

Hartman et al.

[11] Patent Number: 4,532,237

[45] Date of Patent: Jul. 30, 1985

[54] SUBSTITUTED AND BRIDGED PYRIDINES USEFUL AS CALCIUM CHANNEL BLOCKERS

[75] Inventors: George D. Hartman, Lansdale; Brian T. Phillips, Telford, both of Pa.

[73] Assignee: Merck & Co., Inc., Rahway, N.Y.

[21] Appl. No.: 635,954

[22] Filed: Jul. 30, 1984

[51] Int. Cl.$^3$ .................. C07D 265/12; C07D 279/08; C07D 413/12; A01N 43/86

[52] U.S. Cl. .................... 514/226; 514/236; 514/230; 514/231; 544/14; 544/80; 544/89

[58] Field of Search ............. 424/246, 248.51, 248.55; 544/14, 80, 89

[56] References Cited

U.S. PATENT DOCUMENTS 3,337,581   8/1967   Collins .................................. 544/14
4,380,629   4/1983   Yamshita et al. ..................... 544/89

Primary Examiner—John M. Ford
Attorney, Agent, or Firm—Joseph F. DiPrima; Michael C. Sudol

[57] ABSTRACT

Novel substituted and bridged pyridine compounds useful as calcium channel blockers, pharmaceutical compositions thereof, and methods of treatment are disclosed.

10 Claims, No Drawings

SUBSTITUTED AND BRIDGED PYRIDINES USEFUL AS CALCIUM CHANNEL BLOCKERS

BACKGROUND OF THE INVENTION

Substituted dihydropyridines are known to be useful for reducing blood pressure, effecting dilation of the coronary vessels, and preventing urospasms. Typical of such substituted dihydropyridines are those disclosed in U.S. Pat. Nos. 3,923,818; 3,905,970; 4,044,141; 4,237,137; and 4,285,955. The substituted dihydropyridines disclosed in these patents do not include bridged ring structures.

Weller et al., [J. Org. Chem., 48, pp 3061–7 (1983)] disclose 1'-methylspiro[benzofuran-3(2H), 4'-piperdine] as a substructure of morphine which is an early intermediate in a general synthesis of morphine but not possessing exceptional analgesic activity. Weller et al. also teach the preparation of spiro [benzofuran-3(2H), 4'-(1'H)-pyridines] as potential intermediates in a synthesis of morphine but no biological activity of these compounds is reported.

Goldman [Angew. Chem. Int. Ed. Engl., 20, pp. 779–780 (1981)] teaches the preparation of spiro-[benzothiophene-1-oxide, 4'-pyridines] as an intermediate in the preparation of 4,4-disubstituted 1,4-dihydropyridines.

SUMMARY OF THE INVENTION

This invention is directed to novel substituted and bridged pyridines and derivatives thereof and to methods for preparing such compounds. This invention is also directed to pharmaceutical compositions and methods of treatment for cardiovascular disorders in which high cellular concentration of $Ca^{++}$ is a factor.

DETAILED DESCRIPTION OF THE INVENTION

The specific substituted and bridged pyridine compounds of this invention are represented by the following general structural formula (I):

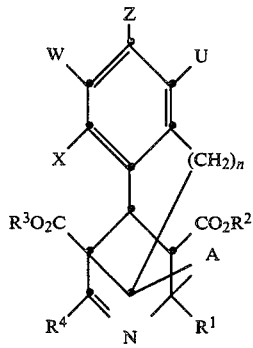

wherein:
n is 0, 1 or 2;
A is oxygen or sulfur;
$R^1$ and $R^4$ independently are hydrogen, $C_1$–$C_8$ alkyl, $C_2$–$C_8$ alkenyl, $C_3$–$C_8$ cycloalkyl, $C_1$–$C_8$ hydroxyalkyl;
$R^2$ and $R^3$ independently are $C_1$–$C_8$ alkyl, $C_2$–$C_8$ alkenyl, $C_3$–$C_8$ cycloalkyl, $C_1$$4$ $C_8$ hydroxyalkyl, $C_1$–$C_8$ dihydroxyalkyl, $C_2$–$C_8$ alkoxyalkyl, $C_3$–$C_8$ alkoxy(alkoxyalkyl), $C_1$–$C_8$ aminoalkyl wherein the amino group is $NR^5R^6$ in which $B^5$ and $R^6$ independently are hydrogen, $C_1$–$C_8$ alkyl, $C_7$–$C_{14}$ phenylalkyl or $R^5$ and $R^6$ together with the N atom form a 5 or 6 membered heterocycle selected from the group consisting of piperidinyl, morpholinyl, thiomorpholinyl, pyrrolidinyl, piperazinyl or N'-$C_1$–$C_4$-alkylpiperazinyl; and X, W, Z and U independently are hydrogen, $C_1$–$C_8$ alkyl, $C_1$–$C_8$ alkoxy, $CF_3$, cyano, nitro or halo, (i.e. fluoro, chloro or bromo) provided that at least two of X, W, Z and U are hydrogen or X and W or W and Z or Z and U together with the phenyl group to which they are attached form a naphthyl or benzoxadiazole group,
and pharmaceutically acceptable salts thereof.

The preferred compounds of this invention are those represented by the general structural formula (I) wherein:
n is 0 or 1;
A is oxygen;
$R^1$ and $R^4$ independently are hydrogen or $C_1$–$C_8$ alkyl;
$R^2$ and $R^3$ independently are $C_1$–$C_8$ alkyl or $C_1$–$C_8$ aminoalkyl wherein the amino group is $NR^7R^8$ in which $R^7$ and $R^8$ independently are hydrogen, $C_1$–$C_8$ alkyl or $C_7$–$C_{14}$ phenylalkyl; and
X, W, Z and U independently are hydrogen, $C_1$–$C_8$ alkoxy, $CF_3$, cyano, nitro or halo provided that at least two of X, W, Z and U are hydrogen.

The most preferred compounds of this invention are those preferred compounds wherein: $R^1$, $R^2$, $R^3$ and $R^4$ independently are $C_1$–$C_8$ alkyl and X, W, Z and U are hydrogen.

The compounds of this invention possess asymmetric centers and thus exist in different isomeric forms. All such forms are included within the scope of this invention. Specifically, the compounds have an asymmetric center at the carbon atom to which the ester moiety, $-CO_2R^2$, is attached. Whenever that ester moiety is below the plane of the piperidine ring (i.e. down) that stereochemical configuration is denoted as the alpha ($\alpha$)-isomer. Similarly, whenever that ester moiety is above the plane of the piperidine ring (i.e. up) that stereochemical configuration is denoted as the beta ($\beta$)-isomer.

Illustrative of the compounds of this invention are the following compounds of the formula (I) which are the $\alpha$-isomer, the $\beta$-isomer or mixtures thereof:

(1) Dimethyl 2,4a,5,9b-tetrahydro-2$\alpha$,4-dimethyl-2,5-methanoindeno(2,1-a)-1,3-oxazine-4a$\alpha$,10-dicarboxylate [Formula (I) where n is 0, A is oxygen, $R^1$, $R^2$, $R^3$ and $R^4$ are methyl and X, W, Z and U are hydrogen];

(2) Dimethyl 4a,5,10,10a-tetrahydro-2$\alpha$, 4-dimethyl-2,5-methano-2H-naphth(2,3-e)-1,3-oxazine-4a$\alpha$, 11-dicarboxylate [Formula (I) where n is 1, A is oxygen, $R^1$, $R^2$, $R^3$ and $R^4$ are methyl and X, W, Z and U are hydrogen]; and (3) Dimethyl 2,4a,5,9b-tetrahydro-2,4-dimethyl-2,5-methanoindeno(2,1-a)-1,3-thiazine-4a,10-dicarboxylate [Formula (I) where n is 0, A is sulfur, $R^1$, $R^2$, $R^3$ and $R^4$ are methyl and X, W, Z and U are hydrogen].

The pharmaceutically acceptable salts are those acid addition salts of non-toxic, pharmaceutically acceptable acids and include salts of inorganic acids such as hydrochloric, hydrobromic, hydroiodic, phosphoric, sulfuric, nitric and the like, and organic acids such as trifluoroacetic and trichloroacetic and the like and include acids related to the pharmaceutically acceptable salts listed in Journal of Pharmaceutical Science, 66, 2 (1977) and incorporated herein by reference.

The compounds of this invention are conveniently prepared from known or readily obtainable starting materials utilizing the general synthetic pathway described below:

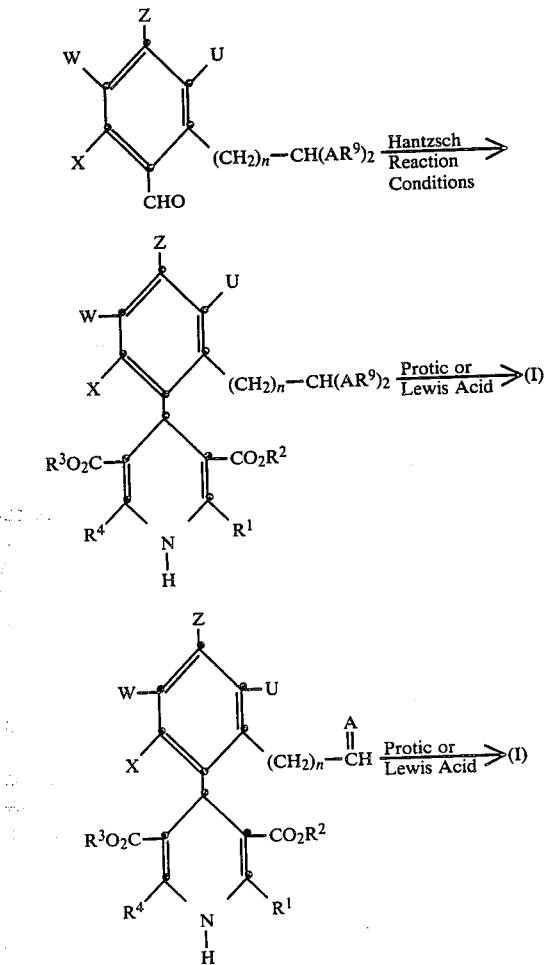

The aryl aldehyde (1), wherein n, A, X, W, Z and U are described above and $R^9$ is $C_1$–$C_4$alkyl, benzyl or both $R^9$'s taken together are ethylene or propylene, is reacted with an appropriately substituted 3-aminopropenoate, such as methyl 3-aminocrotonate, and an appropriately substituted 3-oxo-propanoate, such as methyl acetoacetate, under the general Hantzsch reaction conditions to afford the aryl dihydropyridine compound (2).

The aryl dihydropyridine compound (2) may be treated under mild acidic conditions to remove the acetal or thioacetal protecting group and yield the aryl dihydropyridine compound (3).

The aryl dihydropyridine compound (2) or (3) is then treated at −10° to 50° C., preferably at ambient temperature, with between 0.5 and 5.0 equivalent, preferrably 1.0 equivalents, of either a protic acid or a Lewis acid in an inert solvent to yield the compound of formula (I). Examples of such protic acids and Lewis acids include gaseous hydrogen chloride, gaseous hydrogen bromide, titanium tetrachloride, trimethylsilyl trifluoromethane sulfonate and tin tetrachloride. Exemplifying the inert solvents employed in this cyclization reaction are ethers, chlorinated hydrocarbons and aromatic hydrocarbons. The preferred solvents are methylene chloride, chloroform and benzene.

As indicated above, the compounds of this invention are useful as calcium channel blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory system; (vi) useful antihypercholesterolemic and antilipademic action; (vii) protection of the ischemic myocardium; (viii) inhibition of irritable bowel syndrome and esophageal spasm; and, (ix) inhibition of migraine. Some of these compounds are also useful cardiotonic agents.

The representative compounds of the present invention were found to inhibit vascular calcium contraction, reduce cardiac contractile force, inhibit calcium-mediated tracheal contraction, inhibit calcium uptake in pituitary cells, or displace tritiated nitrendepine from membrane.

The compounds of the present invention can be administered in any suitable form; e.g. orally, sublingually, transdermally, or parenterally; i.e. intravenously, interperitoneally, etc. Thus, the compounds can be offered in a form (a) for oral administration e.q. as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., nitroglycerine tablets, lactose tablets, and the like, for rapid dissolution or high molecular weight methylcellulose tablets, carboxymethylcellulose tablets, and the like, for slower, time-releasing delivery; or, (c) for parenteral administration e.g. dissolved or dispersed in a suitable liquid carrier or emulsified.

The pharmaceutical preparations thus described are made following the conventional techniques of the pharmaceutical chemist as appropriate to the desired end product.

The ratio of active compound to compounding ingredients i.e. carrier, diluent etc. will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or β-blocking agents. For example, the compounds of this invention can be given in combination with such compounds as enalapril, hydralazine hydrochloride, hydrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The following Examples are provided to further illustrate the best mode currently known for preparing the compounds and compositions of this invention, but are not to be construed as limiting this invention in any manner.

EXAMPLE 1

Preparation of Dimethyl 2,4a,5,9b-tetrahydro-2α, 4-dimethyl-2,5-methanoindeno[2,1-a]-1,3-oxazine-4aα,10-dicarboxylate (a) 2-[(1,3-dioxalanyl)]benzaldehyde(1a)

To a solution of 2-bromobenzaldehyde ethylene glycol acetal (190 mmol) in dry tetrahydrofuran (275 ml) at −78° C. under nitrogen was added dropwise n-butyllithium in hexane (190 mmol). The reaction mixture was stirred for an additional 30 minutes and then N-formylpiperidine (210 mmol) in tetrahydrofuran (25 ml) was added dropwise. The reaction mixture was then allowed to warm to ambient temperature over 4 hours. The reaction was quenched with 3N hydrochloric acid to pH of 8 and the reaction mixture diluted with diethyl ether (250 ml). The phases were separated and the aqueous phase extracted with diethyl ether (3×250 ml). The combined organic phase was washed with brine, dried over anhydrous sodium sulfate and filtered. The filtrate was concentrated in vacuo and then fractionated to afford the Compound 1a as a clear oil (bp 95°–100° C.)

(b) Dimethyl 2,6-dimethyl-4-[2-(1,3-dioxalanyl)phenyl]-1,4-dihydropyridine-3,5-dicarboxylate (1b)

To the Compound 1a (16.8 mmol) in dry methanol (10 ml) was added methyl 3-aminocrotonate (16.8 mmol), methyl acetoacetate (16.8 mmol) and concentrated aqueous ammonium hydroxide (1 drop). The reaction mixture was heated under nitrogen at reflux for 24 hours. The solvent was then removed in vacuo and the residue triturated with diethyl ether to afford a yellow solid which was washed with diethyl ether to yield Compound 1b as a white solid (m.p. 235°–7° C. (dec.)).

(c) Dimethyl 2,4a,5,9b-tetrahydro-2α,4-dimethyl-2,5-methanoindeno[2,1-a]-1,3-oxazine-4a,α,10-dicarboxylate To Compound 1b (2.5 mmol) in methylene chloride (50 ml) at ambient temperature was added titanium tetrachloride (1.3 mmol) and lithium iodide (2.8 mmol) and the resulting mixture stirred for 16 hours. The reaction was quenched with water and neutralized with concentrated sodium bicarbonate solution. The organic phase was washed with brine, dried over anhydrous sodium sulfate, and filtered. The filtrate was concentrated in vacuo to give a tan solid which was purified by flash chromatography on silica gel eluted with methanol:chloroform (1:99) to afford the desired product (m.p. 100°–110° C.).

EXAMPLE 2

Preparation of Dimethyl 4a,5,10,10a-tetrahydro-2α4-dimethyl-2,5-methano-2H-naphth[2,3-e]-1,3-oxazine-4aα,11-dicarboxylate (a) 2-(2-Hydroxyethyl)bromobenzene(2a)

To 2-bromophenylacetic acid (46.5 mmol) in dry tetrahydrofuran (50 ml) at −5° C. under nitrogen was added a solution of borane (70 mmol) in tetrahydrofuran dropwise over 45 minutes. The reaction was stirred for an additional hour and then allowed to warm to ambient temperature. The reaction was cooled, quenched with water (10 ml) and the reaction mixture diluted with ethyl acetate (100 ml) and saturated aqueous sodium potassium tartrate (40 ml). The organic phase was separated, washed with saturated sodium bicarbonate solution, brine, dried over anhydrous sodium sulfate and filtered. The filtrate passed through silica gel and then concentrated in vacuo to give the Compound 2a as an oil.

(b) 2-Bromophenylacetaldehyde (2b)

To pyridinium chlorochromate (63 mmol) in methylene chloride (75 ml) at ambient temperature was added a solution of the Compound 2a (45 mmol) in methylene chloride (10 ml) with stirring. The reaction mixture was stirred for 1.5 hour and diluted with diethyl ether (225 ml). The organic phase was separated and the residue triturated with diethyl ether (150 ml). The organic phases were combined, passed through silica gel and the solvent removed in vacuo to give the Compound 2b as an oil.

(c) 2-Bromophenylacetaldehyde ethylene glycol acetal (2c)

To the Compound 2b (40 mmol) in benzene (70 ml) was added ethylene glycol (44 mmol) and p-toluenesulfonic acid monohydrate (100 mg) and the reaction mixture refluxed for 2.5 hours with azeotropic removal of water. The reaction mixture was cooled, extracted with 10% aqueous sodium hydroxide (2×20 ml), water and brine, dried over anhydrous sodium sulfate, and filtered. The filtrate was concentrated in vacuo to afford the Compound 2c as an oil.

(d) 2[2-(1,3-Dioxalanyl)methyl]benzaldehyde (2d)

To the Compound 2c (32 mmol) in dry tetrahydrofuran (40 ml) at −78° C. under nitrogen was added a solution of n-butyllithium (34 mmol) in hexane dropwise. The reaction mixture stirred for an additional hour at −78° C. and then a solution of N-formylpiperidine (32 mmol) in tetrahydrofuran (10 ml) was added dropwise. The reaction mixture was stirred for an additional 2 hours and allowed to warm to ambient temperature overnight. The reaction mixture, cooled in ice, was quenched with saturated aqueous ammonium chloride and diluted with ethyl acetate (60 ml). The organic phase was separated and the aqueous phase extracted with ethyl acetate (60 ml). The combined organic phases were washed with brine, dried over anhydrous sodium sulfate and filtered. The filtrate was concentrated in vacuo to yield a dark oil which was purified by flash chromatography on silica gel eluted with methanol:chloroform (2:98) to afford the desired product as an oil ($R_f$=0.6).

(e) Dimethyl 2,6-dimethyl-4-[2-[2-(1,3-dioxalanylmethyl)]phenyl]-1,4-dihydropyridine-3,5-dicarboxylate (2e)

To the Compound 2d (17.7 mmol) in dry methanol (20 ml) was added methyl 3-aminocrotonate (17.7 mmol), methyl acetoacetate (17.7 mmol) and concentrated ammonium hydroxide (1 drop) and the reaction mixture heated at reflux under nitrogen for 4 days. The solvent was removed in vacuo and the residue purified by flash chromatography on silica gel eluted with methanol:chloroform (2:98) to give a yellow oil ($R_f=0.4$) which was triturated with diethyl ether:hexane (1:1) to afford the desired product as a yellow solid (m.p. 162°–8° C.).

(f) Dimethyl 4a,5,10,10a-tetrahydro-2α,4-dimethyl-2,5-methano-2H-naphth[2,3-e]-1,3-oxazine-4aα,11-dicarboxylate To the Compound 2e (1.5 mmol) in dry diethyl ether (15 ml) and methylene chloride (30 ml) under nitrogen was added titanium tetrachloride (0.75 mmol) and lithium iodide (1.6 mmol) and the reaction mixture stirred at ambient temperature for 3 days. The reaction was quenched with water (3 ml), neutralized with saturated sodium bicarbonate solution and extracted with methylene chloride (3×30 ml). The combined organic extracts were washed with brine, dried over anhydrous sodium sulfate, filtered, and the solvent removed in vacuo. The residue was purified by flash chromatography on silica gel eluted with methanol:chloroform (2:98) to give the 11-α isomer as a solid ($R_f=0.4$, 124°–127.5° C.) and the 11-β isomer as a solid ($R_f=0.3$, m.p. 121°–123° C.).

Alternatively the Compound 2e in methylene chloride was treated with an excess of trimethylsilyl trifluoromethanesulfonate to give the 11-β isomer as the major product and the 11-β isomer as the minor product.

EXAMPLE 3

Preparation of Dimethyl 2,4a,5,9b-tetrahydro-2,4-dimethyl-2,5-methanoindeno[2-a]1,3-thiazine-4a,10α-dicarboxylate To a stirred solution of dimethyl 2,6-dimethyl-4-(2-formylphenyl)-1,4-dihydropyridine-3,5-dicarboxylate (0.1 mmol) in chloroform (40 ml) at ambient temperature was added methanol saturated hydrogen chloride gas (10 ml). Through this solution which was cooled to 0°–5° C. for the first hour was bubbled hydrogen sulfide gas for eight hours. The solvent was removed in vacuo and the residue diluted with water, neutralized with saturated sodium bicarbonate solution and extracted with methylene chloride (2×50 ml). The combined organic phases were dried over anhydrous sodium sulfate, filtered and filtrate concentrated in vacuo to give a yellow solid. The solid was triturated with hexane:diethyl ether (1:4) and then recrystallized from isopropanol to afford the desired product as a solid (m.p. 203°–209° C.).

EXAMPLES 4–20

Utilizing the general procedure of Examples 1, 2 or 3 and starting with appropriately substituted aryl aldehydes the following compounds of the formula (I) are prepared.

| Compound | n | A | $R^1$ | $R^2$ | $R^3$ | $R^4$ | X | W | Z | U |
|---|---|---|---|---|---|---|---|---|---|---|
| 4 | 0 | O | Me | Et | Et | Me | H | H | H | H |
| 5 | 0 | S | Et | Et | Et | Et | H | H | H | H |
| 6 | 0 | O | H | Me | Me | Et | H | OMe | H | H |
| 7 | 0 | O | Me | Me | Me | Me | H | H | H | H |
| 8 | 1 | O | Me | Et | Et | Me | H | $NO_2$ | H | H |
| 9 | 1 | O | Me | Me | Me | Me | H | $CF_3$ | H | H |
| 10 | 2 | O | Me | (cyclohexyl) | (cyclohexyl) | Me | H | H | H | H |
| 11 | 2 | S | Me | Me | Me | Me | H | H | H | H |
| 12 | 1 | O | —CH$_2$CH=CH$_2$ | Me | Me | Me | Cl | Cl | H | H |
| 13 | 2 | O | —CH$_2$OH | Et | Et | Me | H | H | Me | H |
| 14 | 1 | S | (cyclohexyl) | Me | Me | Me | OMe | H | H | H |
| 15 | 1 | O | Me | —CH$_2$CH=CH$_2$ | —CH$_2$CH=CH$_2$ | Me | H | Me | H | H |
| 16 | 2 | S | Me | —CH$_2$CH$_2$OH | Me | Me | H | Cl | H | H |
| 17 | 1 | O | Me | Me | —CH$_2$CH$_2$OCH$_2$CH$_2$OCH$_3$ | Me | H | H | H | F |
| 18 | 1 | S | Me | —CH$_2$CH$_2$NMe$_2$ | —CH$_2$CH$_2$NMe$_2$ | Me | H | $CF_3$ | H | H |
| 19 | 1 | O | Me | —CH$_2$N(CH$_3$)—CH$_2$φ | Et | Me | H | H | H | CN |

| Compound | n | A | R¹ | R² | R³ | R⁴ | X | W | Z | U |
|---|---|---|---|---|---|---|---|---|---|---|
| 20 | 1 | O | Me | CH₂N⟨hexagon⟩ | CH₂N⟨hexagon⟩ | Me | H | H | H | H |

It should be noted that for the preparation of Compounds 13 and 16 the hydroxyalkyl moiety is acylated with acetic anhydride prior to cyclization and then deacylated with sodium hydroxide.

EXAMPLE 21

As a specific embodiment of a composition of this invention an active ingredient, such as dimethyl 2,4a,5,9b-tetrahydro-2α,4-dimethyl-2,5-methanoindeno[2,1-a]-1,3-oxazine-4aα,10α-dicarboxylate, is formulated to yield 5000 compressed tablets, each containing 50 mg of the active ingredient, as follows:

| | |
|---|---|
| Active ingredient | 250 grams |
| Starch | 70 grams |
| Dibasic calcium phosphate hydrous | 500 grams |
| Calcium stearate | 2.5 grams |

What is claimed is:

1. A compound represented by the following general structural formula (I):

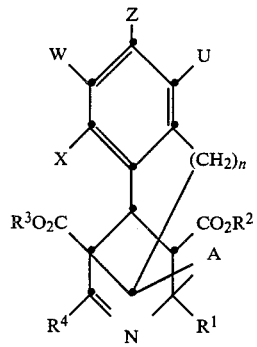

(I)

wherein:

n is 0, 1 or 2;

A is oxygen or sulfur;

R¹ and R⁴ independently are hydrogen, $C_1$-$C_8$ alkyl, $C_2$-$C_8$ alkenyl, $C_3$-$C_8$ cycloalkyl, $C_1$-$C_8$ hydroxyalkyl;

R² and R³ independently are $C_1$-$C_8$ alkyl, $C_2$-$C_8$ alkenyl, $C_3$-$C_8$ cycloalkyl, $C_1$-$C_8$ hydroxyalkyl, $C_1$-$C_8$ dihydroxyalkyl, $C_2$-$C_8$ alkoxyalkyl, $C_3$-$C_8$ alkoxy(alkoxyalkyl), $C_1$-$C_8$ aminoalkyl wherein the amino group is NR⁵R⁶ in which R⁵ and R⁶ independently are hydrogen, $C_1$-$C_8$ alkyl, $C_7$-$C_{14}$ phenylalkyl or R⁵ and R⁶ together with the N atom form a 5 or 6 membered heterocycle selected from the group consisting of piperidinyl, morpholinyl, thiomorpholinyl, pyrrolidinyl, piperazinyl or N'-$C_1$-$C_4$ -alkylpiperazinyl; and X, W, Z and U independently are hydrogen, $C_1$-$C_8$ alkyl, $C_1$-$C_8$ alkoxy, CF₃, cyano, nitro or halo, provided that at least two of X, W, Z and U are hydrogen or X and W or W and Z or Z and U together with the phenyl group to which they are attached form a naphthyl or benzoxadiazole group, or a pharmaceutically acceptable salt thereof.

2. A compound of claim 1 wherein:

n is 0 or 1;

A is oxygen;

R¹ and R⁴ independently are hydrogen or $C_1$-$C_8$ alkyl;

R² and R³ independently are $C_1$-$C_8$ alkyl or $C_1$-$C_8$ amino alkyl wherein the amino group is NR⁷R⁸ in which R⁷ and R⁸ independently are hydrogen, $C_1$-$C_8$ alkyl or $C_7$-$C_{14}$ phenylalkyl; and X, W, Z and U independently are hydrogen, $C_1$-$C_8$ alkoxy, CF₃, cyano, nitro or halo provided that at least two of X, W, Z and U are hydrogen.

3. A compound of claim 2 wherein:

R¹, R², R³ and R⁴ are are independently are $C_1$-$C_8$ alkyl; and X, W, Z, and U are hydrogen.

4. A compound of claim 3 which is dimethyl 2,4a,5,9b-tetrahydro-2α-4-dimethyl-2,5-methanoindeno[2,1-a]-1,3-oxazine-4aα,10-dicarboxylate.

5. A compound of claim 3 which is dimethyl 4a,5,10,10α-tetrahydro-2α,4-dimethyl-2,5-methano-2H-naphth[2,3-e]-1,3 oxazine-4aα,11α-dicarboxylate.

6. A compound of claim 3 which is dimethyl 4a,5,10,10a-tetrahydro-2α-4-dimethyl-2,5-methano-2H-naphth[2,3-e]-1,3-oxazine-4aα-11β-dicarboxylate.

7. A compound of claim 1 which is dimethyl 2,4a,5,9b-tetrahydro-2,4-dimethyl-2,5-methanoindeno[2,1-a]-1,3-thiazine-4a,10α-dicarboxylate.

8. A pharmaceutical composition, useful in the treatment of cardiovascular disorders in which a high cellular concentration of Ca⁺⁺ is a factor, comprising a nontoxic therapeutically effective amount of a compound according to claim 1 in an admixture with a pharmaceutically acceptable carrier.

9. A method of treatment for cardiovascular disorders in which a high cellular concentration of Ca⁺⁺ which comprises administering to a subject in need of such treatment a nontoxic therapeutically effective amount of a compound according to claim 1.

10. A process for the preparation of the compounds of claim 1 which comprises treating a compound of one of the following formulae:

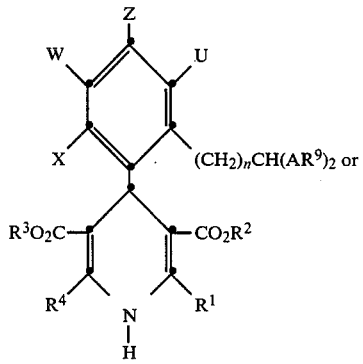

-continued
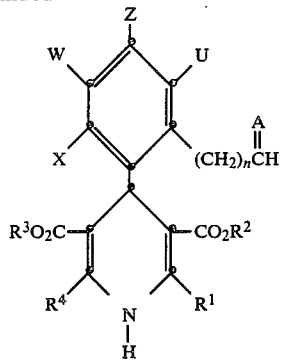
wherein n, A, $R^1$, $R^2$, $R^3$, $R^4$, X, W, Z and U are described in claim 1 and $R^9$ is $C_1$–$C_4$ alkyl, benzyl or both $R^9$'s taken together are ethylene or propylene, with either a protic acid or Lewis acid in an inert solvent.
* * * * *